(12) United States Patent
Ranchon (10) Patent No.: US 9,856,046 B2
(45) Date of Patent: Jan. 2, 2018

(54) HEAT-TREATMENT DEVICE CAPABLE OF RECEIVING LOOSE PRODUCTS (71) Applicant: LAGARDE, Malataverne (FR)

(72) Inventor: Denis Ranchon, Vivier (FR)

(73) Assignee: LAGARDE, Malataverne (FR)

( * ) Notice: Subject to any disclaimer, the term of this patent is extended or adjusted under 35 U.S.C. 154(b) by 299 days.

(21) Appl. No.: 14/381,025

(22) PCT Filed: Mar. 8, 2013

(86) PCT No.: PCT/FR2013/050488
§ 371 (c)(1),
(2) Date: Aug. 26, 2014

(87) PCT Pub. No.: WO2013/135998
PCT Pub. Date: Sep. 19, 2013

(65) Prior Publication Data
US 2015/0013272 A1    Jan. 15, 2015

(30) Foreign Application Priority Data

Mar. 16, 2012 (FR) ...................... 12 52401

(51) Int. Cl.
| B65B 55/14 | (2006.01) |
| A23L 3/10 | (2006.01) |
| A61L 2/00 | (2006.01) |
| A61L 2/04 | (2006.01) |
| B01L 7/02 | (2006.01) |
| B01J 3/04 | (2006.01) |
| B65B 55/18 | (2006.01) |

(52) U.S. Cl.
CPC ............... *B65B 55/14* (2013.01); *A23L 3/10* (2013.01); *A61L 2/0023* (2013.01); *A61L 2/04* (2013.01); *B01J 3/042* (2013.01); *B01L 7/02* (2013.01); *B65B 55/18* (2013.01)

(58) Field of Classification Search
CPC . B65B 55/06; B65B 55/14; A23L 3/10; B01L 7/02
See application file for complete search history.

(56) References Cited

U.S. PATENT DOCUMENTS 3,447,544 A   6/1969  Arriaga Lopez De Vergara
4,003,302 A   1/1977  Mencacci et al.

FOREIGN PATENT DOCUMENTS

| CH | 406810 A | 1/1966 |
| FR | 1036490 A | 9/1953 |
| FR | 2808706 A1 | 11/2001 |

OTHER PUBLICATIONS

International Search Report dated Aug. 21, 2013, corresponding to International Patent Application PCT/FR2013/050488.

*Primary Examiner* — Donald Spamer
(74) *Attorney, Agent, or Firm* — Ladas & Parry LLP (57) ABSTRACT

A heat-treatment device for heat treating packaged products that are available in bulk, and to a method of using the device. The device includes: a chamber; a tank for containing a fluid of a density such that the packaged products float when they are poured in bulk into the fluid, the tank presenting an evacuation compartment for evacuating floating products, the evacuation compartment including a hatch that is suitable for being submerged and then opened so as to evacuate a portion of the fluid including the floating products; fluid supply means for filling the tank and for regulating the level of fluid in the tank; submersion means; recovery means; and reception means.

17 Claims, 5 Drawing Sheets

HEAT-TREATMENT DEVICE CAPABLE OF RECEIVING LOOSE PRODUCTS

This application is a 371 of PCT/FR2013/050488, filed on Mar. 8, 2013, which claims priority to French Application No. 1252401, filed Mar. 16, 2012.

BACKGROUND OF THE INVENTION

The present invention relates to the general field of heat-treatment devices for heat treating packaged products that are available in bulk, said device comprising a chamber for putting under pressure and for performing such a heat treatment by submerging said packages in water heated to a given temperature, in particular sterilizing treatment, in particular in which T=100° C. to 125° C., or pasteurizing treatment, in particular in which T=80° C. to 90° C. Where appropriate, pressurization seeks to keep the water in its liquid state at said temperature, and it also seeks to impart a counter pressure that keeps the packages in shape, which packages would otherwise deform as a result of the heating causing the pressure and the volume of gas contained in the package to increase, where this happens in particular with flexible packages made of plastics material.

Currently, in order to automate a sterilization line upstream and downstream from a heat treatment chamber, also referred to as an autoclave, it is necessary to have specific accessories such as baskets, trays, and/or plates for carrying sterilized products on production lines and/or in the autoclaves, and also a system for conveying, loading, and unloading them. Autoclaves are designed to receive the accessories, baskets, trays, and/or plates in which the products are stored.

Such a system is financially costly. It is also costly in terms of space occupied in factories since the loading and unloading system must be situated in front of or behind the autoclave. Depending on the number of autoclaves, and thus on the number of sets of accessories, a space for storing accessories must also be provided.

In addition, since it is necessary to fill said accessories before conveying them towards and/or into the autoclave, and then to empty them after they have been sterilized, known methods are very costly in terms of production time.

Furthermore, very great attention is required from a maintenance and servicing point of view, so as to avoid mechanical failure. Currently, few solutions exist for providing full automation of the treatment line.

With regard to inspecting treated products, known methods do not make it possible to detect, visually and directly, poor sealing, porosity, and/or leakage of a package.

OBJECT AND SUMMARY OF THE INVENTION

A main object of the present invention is to mitigate the drawbacks of known methods and autoclaves and to simplify heat treatment of products by proposing a heat-treatment device for heat treating packaged products that are available in bulk, said device comprising a chamber for putting under pressure and for performing such heat treatment, said device being characterized in that it further comprises:

- a tank for containing a fluid of a density such that the packaged products (P) float when they are poured in bulk into the fluid, the tank presenting evacuation means for evacuating floating products, the evacuation means including a hatch that is suitable for being submerged and then opened so as to evacuate a portion of the fluid including the floating products (P);
- fluid supply means for filling the tank and for regulating the level of fluid in the tank;
- submersion means (also referred to below as "pressers") that act at the top surface of the fluid present in the tank so as to submerge the bulk products in the fluid;
- recovery means for recovering the products contained within the fluid that is evacuated from the tank when opening the evacuation compartment; and
- reception means for receiving the fluid that pours out when opening the evacuation compartment.

More particularly, said hatch is situated in an end wall, in particular the downstream or front wall in the top portion of the wall of the tank.

Such a heat-treatment device enables loading to take place directly into the tank, typically by mere conveying of the products, making it possible to eliminate completely said accessories and any shuttle systems, feed platforms, etc.

On unloading, it is also possible to deliver the products directly to the outside without any accessories, or shuttle systems, or output platforms, as are currently used.

Substantial savings are made in terms of investment in infrastructure. Furthermore, the novel device makes it possible to save space since it is no longer necessary to provide zones for storing and for handling the accessories.

With regard to productivity times, operations of filling accessories twice are omitted since the products are loaded directly into the tank of the autoclave.

Use is made of simple principles of moving products by causing fluid in the tank to flow within the device of the invention, and this reduces mechanical systems as much as possible.

Furthermore, among additional advantages, the device enables non-sealed defective packages to sink to the bottom of the tank. This makes it possible to see them and to eliminate them by not evacuating them when unloading the floating products. This makes it possible to improve control over the safety of foods.

In a preferred embodiment, said tank is removable and can be inserted into and removed from said chamber via at least one door of said chamber, said tank preferably being suitable for co-operating with movement means such as rails and/or slideways on which it is placed.

It should also be observed that the invention thus requires only minor modifications to currently known autoclave chambers since the tank may be installed on the rails and the other devices used to deliver accessories. The arrangements necessary for putting the tank into place and for performing the invention are thus minor and may be achieved at low cost since the chamber remains a standard chamber. The transformation of the chamber may also be reversed easily, so as to be able to return to a device for treating non-floating products by conventional treatments.

Finally, it should be observed that the chamber is subjected to fewer mechanical stresses since thermal shocks are not applied directly to the body of the chamber but to the tank that can be repaired and/or replaced more easily, and even more so when it is removable and co-operates with movement means such as rails on which it is placed. The lifetime of the metalwork of the chamber is thus extended.

According to an advantageous characteristic, said tank includes an upper compartment referred to as an evacuation compartment, preferably at an end facing a door of the chamber, which evacuation compartment has a wall that forms or includes a said evacuation hatch of the evacuation compartment, said hatch being openable, preferably by pivoting or sliding, said evacuation compartment being arranged such that the quantity of product inside said evacuation compartment facing said hatch is a quantity that is less than that the total quantity of product contained in the tank.

The compartment thus enables the evacuation of the products via said hatch to be controlled better by limiting the quantity of products facing the hatch.

More particularly, said evacuation compartment constitutes an overhanging structure that extends from one of the ends of the tank. The hatch of the evacuation compartment may thus be placed at a longitudinal end of the tank that faces towards an outlet of the chamber, thereby making it easier to manage the evacuation of the treated products.

According to an advantageous characteristic, said upper compartment includes a floor that extends horizontally over the floor of the chamber, and that extends beyond and away from the top of a lower vertical transverse wall of the tank towards the outlet door of the chamber, said lower vertical transverse wall of the tank defining a bottom portion of the tank that lies below and upstream from said evacuation compartment. Thus, as a result of the reduction in the depth of water in the evacuation compartment, the flow of the fluid and of the products that are evacuated via the hatch while it is open is accelerated, thereby enabling better control of the evacuation of the products via said hatch.

In addition, this makes it possible to distinguish a bottom portion of the tank upstream from said evacuation compartment that is deeper than said compartment, within which the products can be submerged completely by means of said pressers, and on the bottom wall of which the non-floating products having damaged packaging can be recovered.

Still more particularly, said hatch of the evacuation compartment is placed at a vertical transverse wall of said evacuation compartment at an end of the tank that is arranged facing an outlet of the chamber.

It should be understood that the transverse end wall of said evacuation compartment constitutes the top portion of the transverse wall of the tank at that end.

The structure of the evacuation compartment overhanging the floor of the chamber on the outside of one of the ends of the tank, also makes it possible to release the space below a portion of the tank for accommodating a reception container for receiving the fluid that separates from the products during evacuation onto said perforated ramp or chute.

Advantageously, the recovery means for recovering the products contained within the fluid that is evacuated from the tank when opening said hatch comprise a sloping ramp or chute that is preferably perforated and that extends outside said tank from just below said hatch, and they are associated with dehumidification or drying means for dehumidifying or drying the products that are evacuated onto said ramp or chute. This characteristic makes it possible to reduce the time required for treatment still further, by combining two steps of the method of treating the products.

In a variant embodiment, the hatch of the evacuation compartment is placed in the underside of the overhanging structure.

Preferably, the hatch of the evacuation compartment is placed in the end of the overhanging structure. With this characteristic, control is easier and the outflow of products is steadier.

According to a particular characteristic of the invention, the mechanical submersion means comprise one or more perforated plates or one or more grids that are suitable for being raised and lowered between an out-of-fluid position and a submerged position, in which submerged position the products trapped below the plate or the grid may be submerged, preferably below said hatch.

This embodiment of the submersion means is particularly simple and effective. It makes it possible to submerge the products mechanically in safe and simple manner.

According to an advantageous characteristic, the fluid supply means comprise fluid inlets, in particular such as return nozzles, that are situated at the end remote from the evacuation compartment, preferably on a said upstream vertical transverse end wall of the tank, preferably also above and below the floor of said evacuation compartment, preferably also at different heights above and below the floor of said evacuation compartment, and are suitable for injecting fluid for directing the floating products towards the evacuation compartment. This characteristic makes it possible to drive the flow of the floating products during their evacuation.

According to an advantageous characteristic, the device includes control means for controlling the opening of the hatch as a function of the water level in the tank and the compartment and/or of the evacuation speed of the products. Such control thus makes it possible to adapt the evacuation speed of the products as a function of their quantity, of their size, or of the arrival of fluid.

Advantageously, said tank includes means that form an openable second bottom wall that is arranged above the first bottom wall, said second bottom wall being suitable for adopting:

a closed position that prevents sunken products or portions of sunken products of a preceding batch that lie on the first bottom wall from mixing with the floating products of a following batch to be heat treated that is submerged in the fluid above the second bottom wall, the non-floating products of said following batch being deposited on said second bottom wall in the closed position; and an open position that makes it possible to allow the non-floating products that previously lay on said second bottom wall to drop onto said first bottom wall.

In said closed position, the first and second bottom walls of said tank define a compartment that is suitable for trapping the non-floating products.

More particularly, said means that form the second bottom wall comprise two pivotable flaps that are hinge mounted on the opposite longitudinal side walls of said tank, above said first bottom wall, said first bottom wall including a second evacuation hatch, said flaps being suitable for floating so that:

when the fluid level is situated below the edges of the flaps fitted with hinges fastened to said longitudinal walls, said flaps are in said open position; and when the fluid level is situated above the edges of the flaps fitted with hinges fastened to said longitudinal walls, said flaps are in said closed position.

The invention also relates to a heat-treatment method for heat treating packaged products that are available in bulk, said method using a chamber for putting the products under pressure, preferably with a device of the invention as defined above, said method being characterized in that it comprises the following steps consisting in:

filling a tank placed in the chamber with fluid;

filling the tank with a batch of packaged products P in bulk, said fluid being of a density such that the packaged products float when they are poured in bulk into said tank, the tank presenting evacuation means for evacuating floating products, said evacuation means including a hatch that is suitable for being submerged;

submerging the products mechanically;
closing the chamber;
proceeding with heat treatment within the chamber by heating the water within said tank and putting the inside of the chamber under pressure;
allowing said products to float upwards;
opening the evacuation hatch for evacuating the floating products;
supplying said tank with fluid and causing the fluid and the products to flow so as to control the evacuation of the fluid and of the products (P) via the hatch;
recovering said products contained within the fluid that is evacuated outside the tank;
recovering the poured out fluid.

More particularly, the method comprises the following steps consisting in:
filling a said tank that presents a said evacuation compartment for evacuating the floating products and that includes a hatch that is suitable for being submerged, with fluid up to a first level that is situated below said hatch;
pouring said products in bulk into the tank;
submerging said products mechanically;
closing said chamber;
proceeding with heat treatment within said chamber;
adding fluid into the tank up to a second level enabling the evacuation compartment and the hatch to be submerged;
allowing said products to float upwards;
opening said hatch of said evacuation compartment for evacuating said floating products;
supplying said tank with said fluid and causing the fluid and the products to flow so as to control the evacuation of the fluid and of said products via the hatch, by controlling the fluid level within said tank while said products are being evacuated;
recovering said products contained within the fluid that is evacuated from the tank;
recovering the poured out fluid.

In an implementation of the method, the following steps are performed in which:
the non-floating products are deposited on means that form a second bottom wall when in a closed position, which second bottom wall is arranged above the first bottom wall, said second bottom wall being suitable for adopting:
a closed position that prevents sunken products or portions of sunken products of a preceding batch that lie on the first bottom wall from mixing with the floating products of a following batch to be heat treated that is submerged in the fluid above the second bottom wall, the non-floating products of said following batch being deposited on said second bottom wall in the closed position; and
an open position that makes it possible to allow the non-floating products that previously lay on said second bottom wall to drop onto said first bottom wall; and
after all of the floating products have been evacuated via said evacuation hatch, said second bottom wall is opened so as to deposit, on said first bottom wall, the non-floating products that previously lay on said second bottom wall.

Advantageously, after several heat-treatment cycles, if necessary, the removable tank is removed from the chamber in order to maintain it or replace it.

An essential advantage of the device and method of the invention resides specifically in using a removable tank that can be removed, making it possible:
to be able to replace it and/or maintain it more easily than the walls of the chamber when it is the chamber that acts as the tank; and
to use the chamber for performing some other type of heat treatment by autoclaving under steam under pressure, for example, by removing said tank.

The ability to replace or handle the removable tank is particularly advantageous since it is said removable tank, and not the walls of the main chamber, that are subjected to mechanical stresses as a result of the pressure inside the chamber and the water temperature inside the tank.

BRIEF DESCRIPTION OF THE DRAWINGS

Other characteristics and advantages of the present invention appear from the following description, given with reference to the accompanying drawings, which show an embodiment that does not have any limiting characteristics. In the figures.

DETAILED DESCRIPTION OF AN EMBODIMENT

Figure 1:
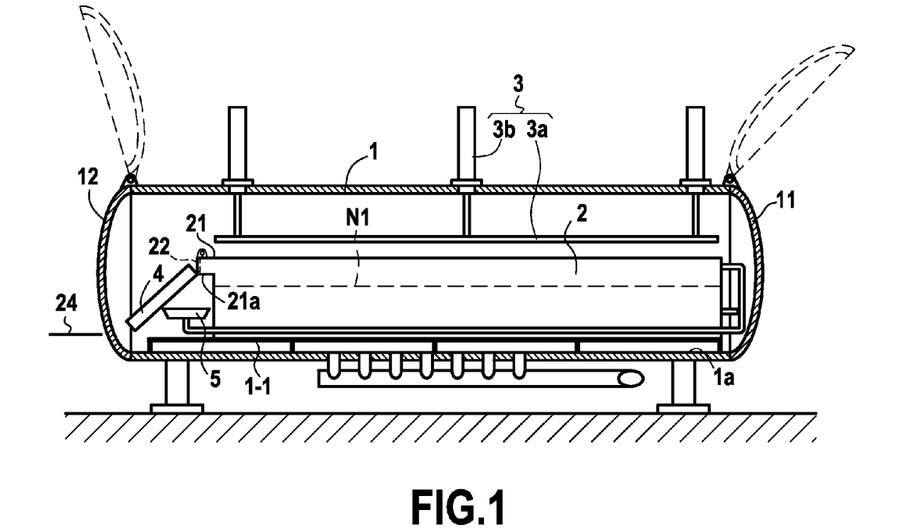
FIG. 1 shows a device of the invention.

FIG. 1 shows a device of the invention. It includes a chamber 1 that is advantageously a conventional autoclave chamber as previously used with accessories. The chamber 1 comprises a substantially-cylindrical body of horizontal longitudinal axis, said body including, at each longitudinal end, an inlet door 11 and an outlet door 12 respectively.

The internal arrangement is modified in accordance with the invention. To do this, an open-topped water tank 2 is installed in removable manner inside the chamber 1 via the inlet or outlet doors 11, 12. Said tank is placed on and is suitable for being moved along rails 2-1. The tank 2 presents a bottom portion having rectangular side walls with a plane or curved bottom wall 2b, said side walls including an upstream transverse end wall 2a-1 facing an inlet door 11 at one end of the chamber 1, and a downstream transverse end wall 2a-2 facing an outlet door 12 at the other end of the chamber 1. The height of the end wall 2a-2 is less than the height of the wall 2a-1. The wall 2a-2 is extended by an overhanging horizontal wall 21a that extends towards the outlet door 12 of the chamber. The wall or floor 21a is terminated by a transverse end wall that forms or includes a pivotable hatch 22 that co-operates with the floor 21a and the ends of the longitudinal side walls of the tank 2 to define an upper compartment of the tank, referred to as an outlet evacuation compartment.

The tank 2 thus includes an overhanging evacuation compartment 21 on one of the ends of the tank 2 positioned beside the outlet door 12.

The evacuation compartment 21 includes a hatch 22 that is situated at the end of the evacuation compartment 21 and thus faces the outlet door 12. However, in an embodiment, the hatch 22 could be integrated in the floor 21a of the evacuation compartment 21. The hatch 22 leads to product recovery means 4, typically a ramp or chute that slopes downwards from the high evacuation compartment 21, towards the floor of the chamber outside the tank.

The ramp or chute for evacuating products P is associated with recovery means for recovering the fluid that pours out with the products P via the hatch into the chute when opening the hatch, said chute including perforations that are suitable for retaining the products P while allowing the fluid to flow away, and fluid reception means 5 that are arranged below the chute, such as a container or the bottom of the chamber 1. The fluid reception means 5 are advantageously coupled with recycling means that recycle the fluid towards the tank for re-use in the treatment method. Typically, the recycled fluid is heated in order to be injected while the tank is being filled for a subsequent treatment cycle, or is injected in a closed circuit via a return nozzle 6 at the upstream transverse end wall 2a-1, so as to cause the products to flow as described below.

Before implementing the method, the water tank 2 is filled up to a first or low level N1. The level N1 is situated below the hatch 22. In this embodiment, since the evacuation compartment overhangs, and since the hatch closes the end of the evacuation compartment 21, the level N1 is thus below the bottom surface 21a of the evacuation compartment 21.

The fluid is then at a constant temperature of several tens of degrees, and is thus advantageously preheated.

Preferably, during this stage, the inlet door 11 is open so as to make it possible to supply the tank 2 with products P coming from outside the chamber 1 and entering into the chamber via the door 11, and the outlet door 12 is closed.

Figure 2:
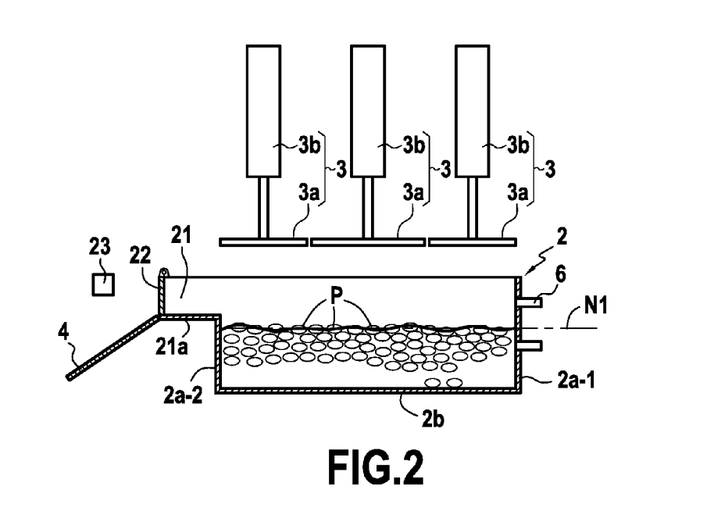
FIG. 2 is a diagram showing the step in the heat-treatment method of pouring products into a device of the invention.

FIG. 2 shows the first step of the heat-treatment method of the invention. The products to be treated P are conveyed and poured in bulk into the water tank 2. Once the suitable quantity of packages for treatment is reached, the inlet door 11 is closed. For example, a tank having a floor 2b with an area lying in the range 5 square meters ($m^2$) to 15 $m^2$, preferably in the range 7 $m^2$ to 8 $m^2$, and having a wall height 2a lying in the range 1 meter (m) to 1.50 m could contain a weight of products lying in the range 5 metric tonnes (t) to 10 t, more particularly in the range 6 t to 8 t, e.g. representing a batch of 10000 to 15000 products P, each of weight lying in the range 100 grams (g) to 250 g arranged in at least three superposed layers in the portion above the floor 2b of the tank 2.

Mechanical submersion means 3 are installed above the open top portion of the tank 2. In this embodiment, the means are perforated horizontal plates or grids 3a having perforations of a size that is smaller than the size of the smallest product that is to be treated in the chamber 1. The submersion plates are moved vertically by means of actuators 3b.

Figure 3:
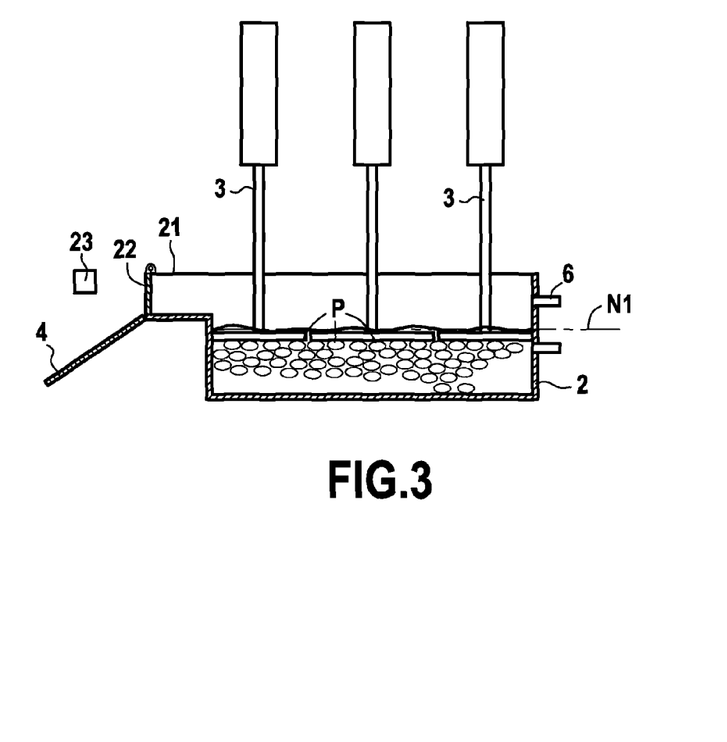
FIG. 3 is a diagram showing the step of submerging products in a heat-treatment method of the invention.

Thus, as shown in FIG. 3, the submersion means 3 are thus actuated, with the products at the surface being forced into a submerged position. The plates are lowered mechanically to just below the level N1, so as to guarantee that all of the products P are completely submerged. This guarantees that all of the products are heat treated when the water is subsequently heated. Thus, the submersion plates are lowered, e.g. by means of actuators having rods that pass through the top of the chamber via tapping holes that typically already exist in existing chambers for steam or other inlets.

In this embodiment, it should be observed that defective packages thus sink naturally to the bottom of the tank as a result of their lack of buoyancy.

The doors 11 and 12 are closed, then the inside of the chamber is put under pressure, e.g. to a pressure lying in the range $10^5$ pascals (Pa) to $5 \times 10^5$ Pa (1 bar to 5 bars), in particular $2 \times 10^5$ to $3.5 \times 10^5$ Pa (2 bars to 3.5 bars).

The heat treatment proper is then performed by heating the water in the tank up to the design temperature, the temperature being maintained for a predetermined submersion time, e.g. 121° C. for 45 minutes (min) to 2 hours (h) so as to sterilize the entire batch of submerged products.

A cooling stage follows for cooling the packages to a desired temperature.

Once the heat-treatment cycle has ended, the contents of the tank 2 are brought to a new level N2 above the floor 21a. This increase in level may be achieved by means of the water inlet that served to fill the tank 2. Advantageously, it is achieved by means of a fluid inlet, typically return nozzles 6 that are situated at the upstream end remote from the evacuation compartment 21 (downstream). The level N2 corresponds to the level at which the evacuation compartment 21 is filled, at least in part, enabling the packages P to be discharged via the open hatch 22 of the evacuation compartment 21 in a lock-gate type system.

Figure 4:
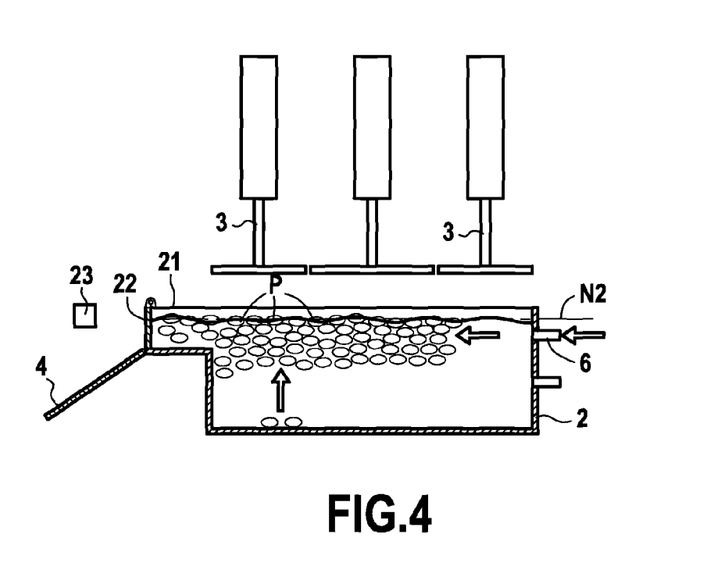
FIG. 4 is a diagram showing the step of de-submerging products after the heat treatment in a device of the invention.

FIG. 4 shows the tank after reaching level N2 during the step of raising the submersion plates 3 shown by the arrows. The products P are thus free to float and they rise naturally to the surface of the fluid in the tank 2. The first packages that rise to the surface are thus directed towards the evacuation compartment 21 by a current of water generated by the return nozzles 6.

Figure 5:
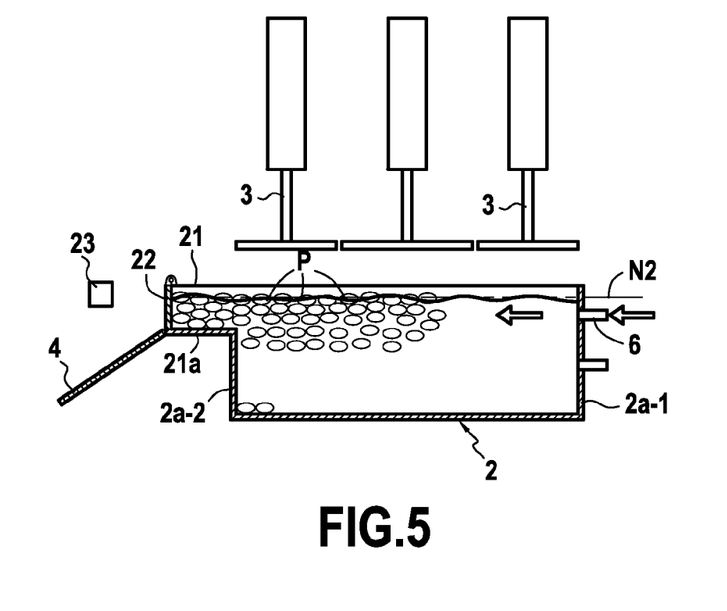
FIG. 5 is a diagram showing the step of pushing the products towards the evacuation compartment, in a device of the invention.

FIG. 5 shows that the downstream evacuation compartment 21 makes it possible firstly to limit the quantity of products facing the hatch 22 at the end of the step of pushing the products P.

Then, the outlet door 12 may be opened while the inlet door 11 remains closed, and the hatch 22 of the evacuation compartment 21 is opened and the first packages begin to fall onto a chute 4 that recovers the products P in the flow of fluid.

Figure 6:
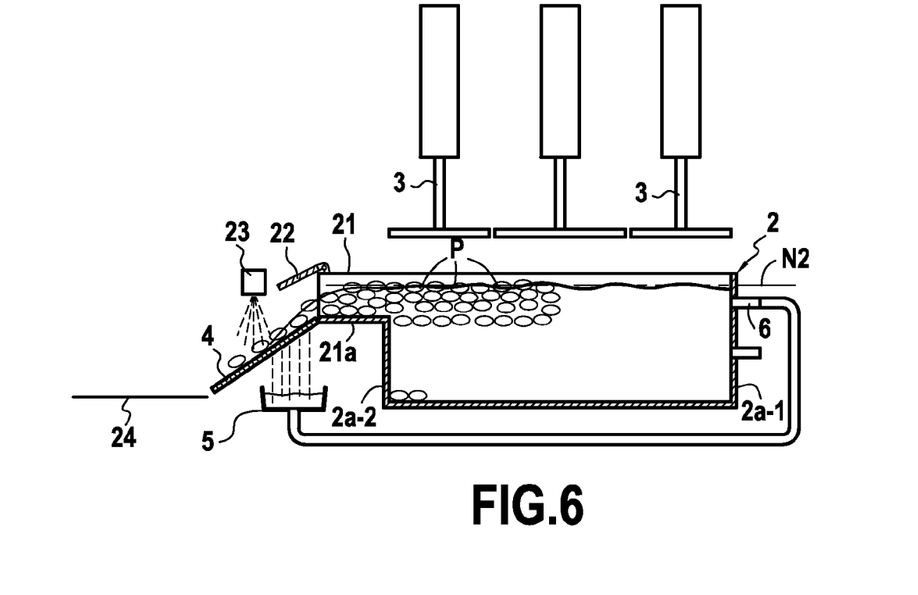
FIG. 6 is a diagram showing the step of evacuating products in a heat-treatment method of the invention.

On Archimedes' principle, the following packages thus rise to the surface in the evacuation compartment 21, and they are also entrained by the current of water maintained by the nozzles 6 towards the evacuation compartment 21. This step is shown in FIG. 6 which shows another advantageous technical effect of the evacuation compartment 21 which, as a result of its height being smaller than the total height of the tank, makes it possible to accelerate the flow rate of the products and fluid leaving via the hatch 22.

In this embodiment, the fluid that is evacuated with the packages is recovered in a container 5 that is placed on the bottom of the chamber 1 or else it is recovered directly in the bottom of the chamber that receives the fluid below the chute 4 and advantageously recycles it for injecting into the tank 2 via the return nozzles 6. A portion of the water may also be recovered for heating and then injecting during a following cycle. This makes it possible to preserve the level N2 and the current of water necessary for continuously evacuating the products P.

Advantageously, the chute 4 is associated with dehumidification means 23 on the outlet path for the packages from the chamber 1, e.g. means for blowing air onto the products P, said means 23 thus being arranged above the ramp 4. This avoids having to provide a special path for dehumidification.

Figure 7:
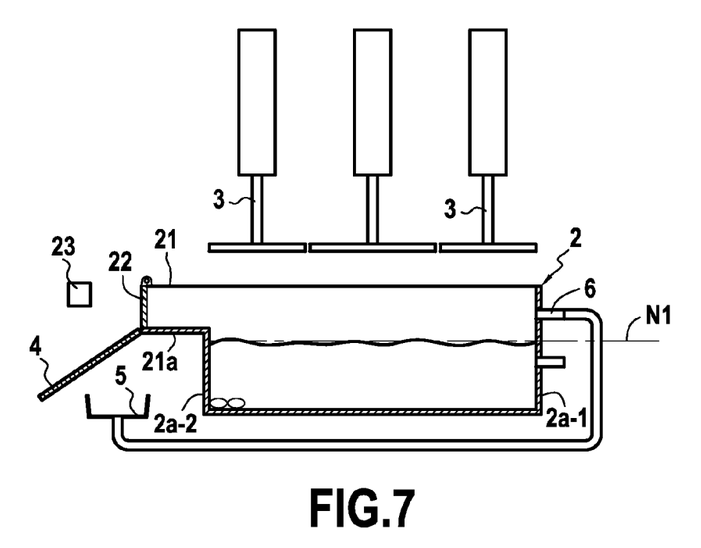
FIG. 7 is a diagram showing the end of the heat-treatment method of the invention.

FIG. 7 is a diagram showing the water tank 2 after the products P have been evacuated and after stopping the operation of the return nozzles 6. All of the packages having a sealing problem as a result of a failure in sealing, in heat-sealing, or in adhesive-bonding, remain at the bottom 2b of the tank 2. Quality control is thus quicker and easier at the outlet of the heat-treatment device.

The fluid level is returned to its initial level N1. The hatch 22 is thus closed and the device is ready to receive a new load of products in bulk.

Advantageously, the fluid used is water. The device of the invention is particularly suitable for flexible packages, but it may also be used for sealed trays and other packages that can be subjected to a heat treatment, and having a density that is compatible with floating in the fluid used in the device of the invention.

An auxiliary hatch situated in the bottom of the water tank 2 is advantageously installed so as to be able to recover the packages that have sunk to the bottom of the tank 2, e.g. with a rake or some other tool.

Finally, it should be observed that various embodiments may be made in accordance with the principles of the invention. In particular, the hatch could be installed in the bottom surface 21a of the evacuation compartment.

In addition, the floor 21a could be eliminated and the hatch 22 could be arranged on the top portion of a raised transverse end wall 2a-2. But this would require accurate control of hatch opening and of the rates at which the tank is filled and products are evacuated.

Figure 8:
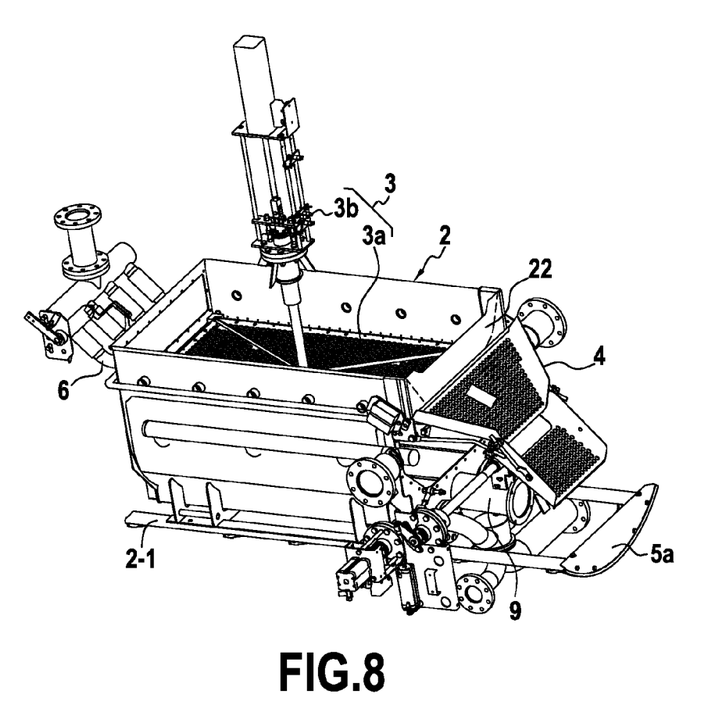
FIG. 8 shows a variant embodiment of the device without the chamber.

In FIG. 8, the device includes skids 1-1 that are suitable for co-operating with rails 2-1 that are arranged on the bottom 1a of the chamber. The device includes a single presser 3 with a large perforated plate 3a that covers the entire area of the tank upstream from the evacuation compartment (the step in the front end wall of the tank forming the evacuation compartment 21 is not visible since it is hidden by the hatch 22). In addition, the fluid is recovered directly in the bottom of the chamber, said chamber being defined by a retaining metal sheet, having a bottom of curved shape that matches the sectional shape of the bottom of the chamber. Said retaining metal sheet 5a is situated downstream from the chamber so as to make it possible to hold the fluid in the bottom of the chamber when the downstream door 12 of the chamber is open so as to make it possible to evacuate the products onto a conveyor 24 outside the chamber.

Figure 9A:
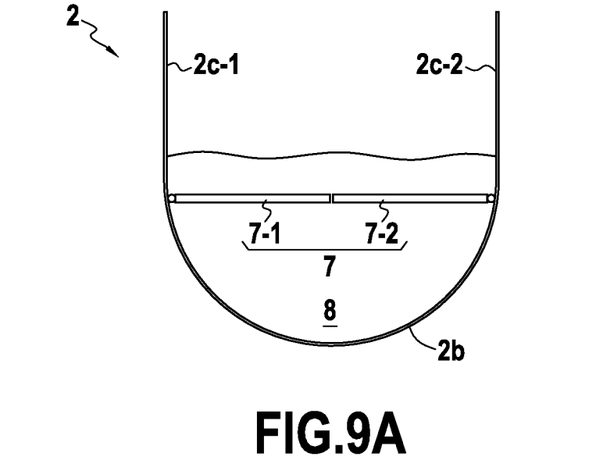
FIGS. 9A and 9B are diagrams in vertical cross-section showing the tank fitted with pivotable flaps that are suitable for forming a second bottom wall 7 above a first bottom wall having a curved section.
Figure 9B:
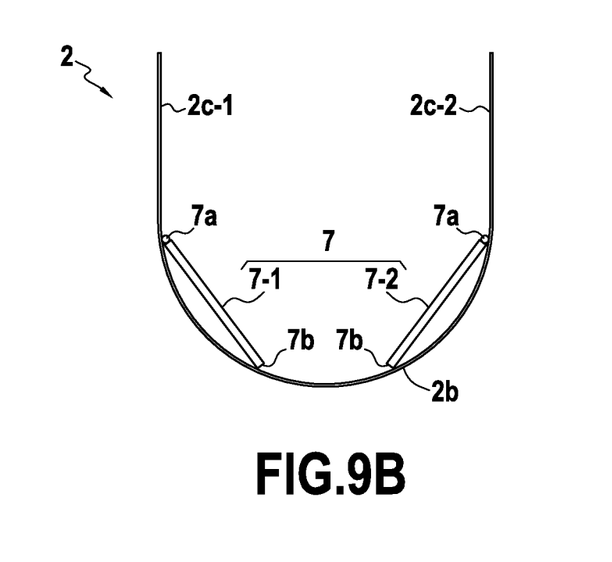

FIGS. 9A and 9B show an embodiment in which the tank 2 is fitted with a double bottom wall, the first bottom wall 2b being surmounted by an openable second wall 7 that is constituted by two pivotable flaps 7-1, 7-2 that are mounted, facing each other, on the two longitudinal side walls 2c-1, 2c-2 of the tank. Said flaps are pivotally hinged in such a manner that the edges 7b of the two flaps meet, on the vertical axial mid-plane of the tank so as to form said double bottom wall, by means of the flaps pivoting about hinges having horizontal pivot axes that are fastened to the walls 2c-1, 2c-2, and that are secured to the opposite edges 7a beside said opposite longitudinal side walls 2c-1 and 2c-2. In addition, the flaps have floats. In this embodiment, the floating flaps are fastened to the walls of the tank and pivot towards the middle, but they could also be fastened about an axis at the middle of the tank and pivot on either side towards the walls.

Thus, in the absence of fluid in the tank, FIG. 9B, the flaps are in their open low position, the edges 7b being in contact with the walls 2c-1, 2c-2 respectively, and when the tank is filled with fluid up to a level situated above the flaps, the flaps are closed in their high position. The two flaps in the closed high position of the double bottom wall, FIG. 9A, co-operate with the bottom wall 2b to define a compartment 8 that serves to capture any non-floating products that have sunk.

This capture compartment 8 makes it possible to confine the sunken products of a first treatment, and thus avoid their packaging and/or their content mixing with the products to be treated during a subsequent treatment of a second batch of products. It also makes it possible to store the sunken products resulting from various batches in said capture compartment 8 that is subsequently evacuated by means of a second hatch 9 in the bottom wall 2b. This makes it possible to avoid evacuating sunken products from a preceding batch before treating a following batch. Without a capture compartment, there is a risk that the sunken packages become separated from their contents and mix into the fluid with the products to be treated of a following batch.

The invention claimed is:

1. A heat-treatment device for heat treating products that are packaged and available in bulk, said device comprising a chamber for putting under pressure and for performing such heat treatment, said device comprising:
    a tank for containing a fluid of a density such that the products float when poured in bulk into the fluid, the tank presenting evacuation means for evacuating products which are floating, the evacuation means including an evacuation compartment comprising an evacuation hatch that is suitable for being submerged and then opened so as to evacuate, from the evacuation compartment, a portion of the fluid including the products which are floating;
    fluid supply means for filling the tank and for regulating the level of fluid in the tank;
    mechanical submersion means that act at the top surface of the fluid present in the tank so as to submerge the products in the fluid;
    recovery means for recovering the products contained within the fluid that is evacuated from the tank when opening the evacuation hatch; and
    reception means for receiving the fluid that pours out when opening the evacuation hatch.

2. The device according to claim 1, wherein said tank is removable and can be inserted into and removed from said chamber via at least one door of said chamber.

3. The device according to claim 2, wherein said tank is suitable for co-operating with movement means comprising rails and/or slideways on which said tank is placed.

4. The device according to claim 1, wherein said evacuation compartment is an upper compartment, and wherein said evacuation compartment has a wall that forms or includes said evacuation hatch of the evacuation compartment, said evacuation hatch being openable, by pivoting or sliding.

5. The device according to claim 4, wherein the evacuation compartment constitutes an overhanging structure that extends from one longitudinal end of the tank.

6. The device according to claim 5, wherein said evacuation compartment includes a floor that extends horizontally over a main floor of the tank, beyond and away from the top of a lower vertical transverse wall of said tank towards an outlet door of the chamber, said lower vertical transverse wall of the tank defining a bottom portion of the tank that lies below and upstream from said evacuation compartment.

7. The device according to claim 4, wherein said evacuation hatch is placed at a vertical transverse wall of said evacuation compartment at an end of the tank that is arranged facing an outlet of the chamber.

8. The device according to claim 4, wherein the fluid supply means comprises fluid inlets that are situated at a longitudinal end of the tank, remote from the evacuation compartment and that inject fluid for directing the products towards the evacuation compartment.

9. The device according to claim 4, wherein the device includes a control means for controlling the opening of said evacuation hatch as a function of the water level in the tank and the evacuation compartment, and/or of the evacuation speed of the products.

10. A device according to claim 4, wherein said evacuation compartment is configured so that the quantity of products inside said evacuation compartment facing the evacuation hatch can be less than the total quantity of products contained in the tank.

11. The device according to claim 1, wherein the mechanical submersion means comprises at least one perforated plate, or at least one grid that is suitable for being raised and lowered between an out-of-fluid position and a submerged position, in which submerged position, the products trapped below on of the at least one plate or on of the at least one grid may be submerged, below said evacuation hatch.

12. The device according to claim 1, wherein the recovery means for recovering the products contained within the fluid that is evacuated from the tank when opening said evacuation hatch comprises a sloping ramp or chute and that extends outside said tank from just below said evacuation hatch, and the recovery means is associated with dehumidification or drying means for dehumidifying or drying the products that are evacuated onto said ramp or chute.

13. The device according to claim 1, wherein said tank includes a means that forms an openable second bottom wall that is arranged above a first bottom wall, said second bottom wall being suitable for adopting:
  a closed position that prevents products which are non-floating or portions of products which are non-floating of a preceding batch that lie on the first bottom wall from mixing with products which are floating of a following batch to be heat treated that is submerged in the fluid above the second bottom wall, the products which are non-floating which are of said following batch being deposited on said second bottom wall in the closed position; and
  an open position that makes it possible to allow the products which are non-floating that previously lay on said second bottom wall to drop onto said first bottom wall.

14. The device according to claim 13, wherein said means that form the second bottom wall comprise two pivotable flaps that are hinge mounted on two opposite longitudinal side walls of said tank, above said first bottom wall, said first bottom wall including a second evacuation hatch, said flaps being suitable for floating so that:
  when the fluid level is situated below edges of the flaps fitted with hinges fastened to said longitudinal side walls, said flaps are in said open position; and
  when the fluid level is situated above the edges of the flaps fitted with hinges fastened to said longitudinal side walls, said flaps are in said closed position.

15. A heat-treatment method for heat treating products that are packaged and available in bulk, said method using a chamber for putting the products under pressure, with a device according to claim 1, said method comprising the following steps:
  a) filling the tank placed in the chamber with fluid;
  b) filling the tank with a batch of products in bulk, said fluid being of a density such that the products float when they are poured in bulk into said tank, the tank presenting the evacuation means for evacuating products which are floating, said evacuation means including the evacuation hatch that is suitable for being submerged;
  c) submerging the products mechanically;
  d) closing the chamber;
  e) proceeding with heat treatment within the chamber by heating the fluid within said tank and putting the inside of the chamber under pressure;
  f) allowing said products to float upwards;
  g) opening the evacuation hatch for evacuating floating products;
  h) supplying said tank with fluid and causing the fluid and/or the products to flow so as to control an evacuation of the fluid and of the products via the evacuation hatch;
  i) recovering said products contained within the fluid that is evacuated outside the tank; and
  j) recovering the poured out fluid.

16. The method according to claim 15, wherein:
said tank presents an evacuation compartment for evacuating the floating products and includes the evacuation hatch that is suitable for being submerged, with fluid up to a first level that is situated below said evacuation hatch;
in step b), the products are poured in bulk into the tank;
in step b), adding fluid into the tank up to a second level enabling the evacuation compartment and the evacuation hatch to be submerged; and
in step h), supplying said tank with said fluid and causing the fluid and/or the products to flow so as to control the evacuation of the fluid and of the products via the evacuation hatch, by controlling the fluid level within the tank while the products are being evacuated.

17. The method according to claim 15, wherein:
products which are non-floating are deposited on a means that forms a second bottom wall when in a closed position, which second bottom wall is arranged above a first bottom wall, said second bottom wall being suitable for adopting:
  a closed position that prevents products which are non-floating, or portions of products which are non-floating, of a preceding batch that lie on the first bottom wall from mixing with products which are floating of a following batch to be heat treated that is submerged in the fluid above the second bottom wall, the products which are non-floating of said following batch being deposited on said second bottom wall in the closed position; and
  an open position that makes it possible to allow the products which are non-floating that previously lay on said second bottom wall to drop onto said first bottom wall; and
  after all of the products which are floating have been evacuated via said evacuation hatch, said second bottom wall is opened so as to deposit, on said first bottom wall, the products which are non-floating that previously lay on said second bottom wall.

\* \* \* \* \*